United States Patent [19]

Liotta

[11] Patent Number: 5,276,151
[45] Date of Patent: Jan. 4, 1994

[54] METHOD OF SYNTHESIS OF 1,3-DIOXOLANE NUCLEOSIDES

[75] Inventor: Dennis C. Liotta, Stone Mountain, Ga.

[73] Assignee: Emory University, Atlanta, Ga.

[21] Appl. No.: 803,028

[22] Filed: Dec. 6, 1991

Related U.S. Application Data

[63] Continuation of Ser. No. 659,760, Feb. 22, 1991, which is a continuation-in-part of Ser. No. 473,318, Feb. 1, 1990, and a continuation of Ser. No. 736,089, Jul. 26, 1991.

[51] Int. Cl.$^5$ .................. C07D 239/02; C07D 407/04
[52] U.S. Cl. .................................. 544/317; 544/225; 544/229; 544/262; 544/265; 544/276; 544/277; 544/310; 544/313; 544/314; 549/214
[58] Field of Search ............... 544/276, 277, 313, 314, 544/317, 225, 229, 265, 264, 310; 549/214

[56] References Cited

U.S. PATENT DOCUMENTS

| | | | |
|---|---|---|---|
| 5,041,449 | 8/1991 | Belleau et al. | 514/274 |
| 5,047,407 | 9/1991 | Belleau et al. | 514/274 |

FOREIGN PATENT DOCUMENTS

| | | | |
|---|---|---|---|
| 382526 | 8/1990 | European Pat. Off. | 514/274 |

OTHER PUBLICATIONS

Bartlett, J. Am. Chem. Soc. 1983, 105, 2088–2089.
Annunziata et al, Tetrahedron Lett. vol. 31, No. 46, pp. 6733–6736 (1990).
Willson et al, Tetrahedron Lett. vol. 31, No. 13, pp. 1815–1818 (1990).
Choi, W., et al., "In Situ Complexation Directs the Stereochemistry of N-Glycosylation in the Synthesis of Oxathiolanyl and Dioxolanyl Nucleoside Analogues," J. Amer. Chem. Soc., 113(24) (1991) 9377–9379.
Evans, D. A., et al., "New Procedure for the Direct Generation of Titanium Enolates, Diastereoselective Bond Constructions with Representative Electrophiles," J. Amer. Chem. Soc., 112 (1990) 8215–8216.

Primary Examiner—Cecilia Tsang
Attorney, Agent, or Firm—Kilpatrick & Cody

[57] ABSTRACT

A synthesis of 1,3-dioxolane nucleosides that includes condensing a 2-0-protected-5-0-acylated-1,3-dioxolane with a purine or pyrimidine base in the presence of a titanium containing Lewis acid to provide predominately the desired β-isomer in the C1'-position of a 1,3-dioxolane nucleoside.

A process for the resolution of a racemic mixture of 1,3-dioxolane nucleoside enantiomers is also disclosed that includes the step of exposing the racemic mixture to an enzyme that preferentially catalyzes a reaction in one of the enantiomers.

10 Claims, 2 Drawing Sheets

1, 3 - Dioxolane Nucleoside wherein:

B = purine or pyrimidine base

X = C4' chiral carbon atom

Y = C1' chiral carbon atom

METHOD OF SYNTHESIS OF 1,3-DIOXOLANE NUCLEOSIDES

The U.S. Government has rights in this invention arising out of National Institutes of Health Grant No. AI-28731 and No. AI-26055.

This application is a continuation of U.S. Ser. No. 07/659,760 filed Feb. 22, 1991, which is a continuation-in-part of U.S. Ser. No. 07/473,318, filed on Feb. 1, 1990. The application is also a continuation of U.S. Ser. No. 07/736,089, filed Jul. 26, 1991. The contents of both of these applications are incorporated by reference.

BACKGROUND OF THE INVENTION

This invention is in the area of organic chemistry, and in particular provides a stereoselective synthesis of 1,3-dioxolane nucleosides.

In 1981, acquired immune deficiency syndrome (AIDS) was identified as a disease that severely compromises the human immune system, and that almost without exception leads to death. In 1983, the etiological cause of AIDS was determined to be the human immunodeficiency virus (HIV). In December, 1990, the World Health Organization estimated that between 8 and 10 million people worldwide were infected with HIV, and of that number, between 1,000,000 and 1,400,000 were in the United States.

In 1985, it was reported that the synthetic nucleoside 3'-azido-3'-deoxythymidine (AZT) inhibits the replication of human immunodeficiency virus type 1. Since then, a number of other synthetic nucleosides, including 2', 3'-dideoxyinosine (DDI), 2',3'-dideoxycytidine (DDC), 3'-fluoro-3'-deoxythymidine (FLT), 2', 3'-dideoxy,2', 3'-didehydrothymidine (D4T), and 3'-azido-2', 3'-dideoxyuridine (AZDU), have been proven to be effective against HIV. A number of other 2', 3'-dideoxynucleosides have been demonstrated to inhibit the growth of a variety of other viruses in vitro. It appears that, after cellular phosphorylation to the 5'-triphosphate by cellular kinases, these synthetic nucleosides are incorporated into a growing strand of viral DNA, causing chain termination due to the absence of the 3'-hydroxyl group.

Both DDC and D4T are potent inhibitors of HIV replication with activities comparable (D4T) or superior (DDC) to AZT. However, both DDC and D4T are not efficiently converted to the corresponding 5'-triphosphates in vivo and are resistent to deaminases and phosphorylases. Both compounds are also toxic.

The success of various 2', 3'-dideoxynucleosides in inhibiting the replication of HIV in vivo or in vitro has led a number of researchers to design and test nucleosides that substitute a heteroatom for the carbon atom at the 3'-position of the nucleoside. Norbeck, et al., disclose that (±)-1-[(2β, 4β)-2-(hydroxymethyl)-4-dioxolanyl]thymine (referred to below as (±)-dioxolane-T or DOT, see FIG. 2), a 1,3 dioxolane nucleoside, exhibits a modest activity against HIV ($EC_{50}$ of 20 μm in ATH8 cells), and is not toxic to uninfected control cells at a concentration of 200 μm. Tetrahedron Letters 30 (46), 6246, (1989). In light of the fact that this compound exhibits efficacy against HIV and has very low toxicity, it is desirable to develop suitable synthetic protocols for preparing a wide variety of analogs and isomers of this compound.

To market a nucleoside for pharmaceutical purposes, it must not only be efficacious with low toxicity, it must also be cost effective to manufacture. An extensive amount of research and development has been directed toward new, low cost processes for large scale nucleoside production. 2', 3'-Dideoxynucleosides are currently prepared by either of two routes; derivatization of an intact nucleoside or condensation of a derivatized sugar moiety with a heterocyclic base. Although there are numerous disadvantages associated with obtaining new nucleoside analogues by modifying intact nucleosides, a major advantage of this approach is that the appropriate absolute stereochemistry has already been set by nature. Obviously, this approach cannot be used in the production of nucleosides that contain either nonnaturally occurring bases or nonnaturally occurring carbohydrate moieties (and which therefore are not prepared from intact nucleosides), such as 1,3-dioxolane nucleosides.

When condensing a carbohydrate-like moiety such as a 1,3-dioxolane with a heterocyclic base to form a synthetic nucleoside, a nucleoside is produced that has two chiral centers (at the C1' and C4' positions, see FIG. 1), and thus exists as a diastereomeric pair. Each diastereomer exists as a set of enantiomers. Therefore, the product is a mixture of four enantiomers. It is often found that nucleosides with nonnaturally-occurring stereochemistry in either the C1' or the C4'-positions are less active than the same nucleoside with the stereochemistry as set by nature.

It is well known in the art that the stereoselective introduction of bases to the anomeric centers of carbohydrates can be controlled by capitalizing on the neighboring group participation of a 2-substituent on the carbohydrate ring [Chem. Ber. 114:1234 (1981)]. However, dioxolanes do not possess an exocyclic 2-substituent and, therefore, cannot utilize this procedure unless additional steps to introduce a functional group that is both directing and disposable are incorporated into the synthesis. These added steps would lower the overall efficiency of the synthesis.

It is also well known in the art that "considerable amounts of the undesired β-nucleosides are always formed during the synthesis of 2'-deoxyribosides" [Chem. Ber. 114:1234, 1244 (1981)]. Furthermore, this reference teaches that the use of simple Friedel-Crafts catalysts like $SnCl_4$ in nucleoside syntheses produces undesirable emulsions upon the workup of the reaction mixture, generates complex mixtures of the α and β-isomers, and leads to stable δ-complexes between the $SnCl_4$ and the more basic silylated heterocycles such as silylated cytosine. These complexes lead to longer reaction times, lower yields, and production of the undesired unnatural N-3-nucleosides.

Therefore, it is an object of the present invention to provide a method for the synthesis of a variety of 1,3-dioxolane nucleosides that includes condensing a 1,3-dioxolane moiety with a purine or pyrimidine base through a process that provides high β-stereoselectivity at the C1' position.

It is another object of the present invention to provide a method for the resolution of racemic mixtures of 1,3-dioxolane nucleosides at the C4'-position.

SUMMARY OF THE INVENTION

The present invention is a method for the synthesis of 1,3-dioxolane nucleosides that includes condensing a suitably protected 1,3-dioxolane moiety with a heterocyclic base, typically a purine or pyrimidine base, to provide a 1,3-dioxolane nucleoside with high β- stereoselectivity in the C1'-position. The method can be used to prepare the C1-β anomer of biologically active 1,3-dioxolane nucleosides such as 2'-deoxy-5-fluoro-3'-oxacytidine (FDOC), 2'-deoxy-3'-oxacytidine (DOC), and 2'-deoxy-3'-oxathymidine (DOT). The method includes condensing a protected 1,3-dioxolane with a suitably protected purine or pyrimidine base in the presence of a titanium-based Lewis acid of the structure:

$$TiX_nY_{m-n}$$

wherein m=4; n=2, 3, or 4; Ti=titanium; X=Cl, Br, or I; and Y is alkoxy, aryloxy, amino, alkylamino, dialkylamino, mixtures thereof, or a bifunctional molecule that contains both an alkoxy and an amino functional group and that is bound to the titanium molecule by both the alkoxy and amino moieties.

A process for the resolution of a racemic mixture of 1,3-dioxolane nucleoside enantiomers is also disclosed that includes the step of exposing the racemic mixture to an enzyme that preferentially catalyzes a reaction in one of the enantiomers. The process can be used to resolve a wide variety of 1,3-dioxolane nucleosides, including pyrimidine and purine nucleosides that are optionally substituted in the carbohydrate moiety or base moiety. The resolution of 1,3-dioxolane nucleosides can be performed on large scale at moderate cost.

DETAILED DESCRIPTION OF THE INVENTION

As used herein, the term "enantiomerically enriched nucleoside" refers to a nucleoside composition that includes at least 95% of a single enantiomer of that nucleoside.

As used herein, the term FDOC refers to 2'-deoxy-5-fluoro-3'-oxacytidine, also known as 2-hydroxymethyl-5-(5-fluorocytosin-1-yl)-1,3-dioxolane.

As used herein, the term DOC refers to 2'-deoxy-3'-oxacytidine, also known as 2-hydroxymethyl-5-(cytosin-1-yl)-1,3-dioxolane.

As used herein, the term DOT or dioxolane-T refers to 2'-deoxy-3'-oxathymidine, also known as 2-hydroxymethyl-5-(thymidin-1-yl)-1,3-dioxolane.

As used herein, the term "preferential enzyme catalysis" refers to catalysis by an enzyme that favors one substrate over another.

As used herein, the term "dioxolane prodrug analogue" refers to a 5'-oxyacyl or H substituted and/or N4 alkyl, substituted alkyl, cycloalkyl or acyl substituted 2'-deoxy-3'-oxo nucleoside that metabolizes to the same active component or components as a dioxolane nucleoside.

Figure 1:
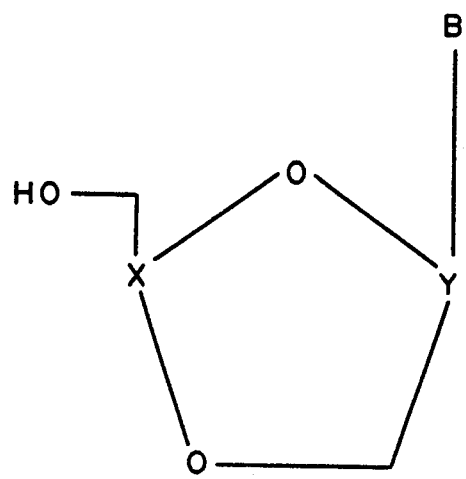
FIG. 1 is an illustration of the chemical structure of a 1,3-dioxolane nucleoside that indicates the position of the two chiral carbon atoms (C1' and C4') in the molecule.

As used herein, the term "1,3-dioxolane nucleoside" refers to a nucleoside in which a purine or pyrimidine base is attached to a 1,3-dioxolane ring through the C5 carbon of the dioxolane (which becomes the C1'-carbon of the nucleoside), as shown in FIG. 1.

As used in this application, the term "predominately" means greater than 80%.

As used herein, the term "protected" means that the functional group, that typically includes an oxygen or nitrogen atom, has been protected by any method known to those skilled in the art for the protection of that group.

As used herein, the term "acylation" means replacement of an H in a functional group of interest with XC(O), wherein X is an alkyl or aromatic group, typically a lower alkyl (C5 or less).

As used herein, the term "alkoxy" refers to an alkyl—O—moiety, wherein the alkyl group can be straight chain, branched, or cyclic.

As used herein, the term "aryloxy" refers to $C_6H_5$—O—, or a derivative thereof in which there is one or more hydrocarbon, halo, or other substituents on the aromatic ring.

As used herein, the term "alkylamino" refers to alkyl—NH—, wherein the alkyl group is straight chain, branched, or cyclic.

As used herein, the term "dialkylamino" refers to $(alkyl)_2N$—, wherein the alkyl group is straight chain, branched, or cyclic.

As used herein, the term "arylamino" refers to $C_6H_5$—NH—, or a derivative thereof in which there is one or more hydrocarbon, halo, or other substituents on the aromatic ring.

As used herein, the term "diarylamino" refers to $(C_6H_5)_2$—N—, or a derivative thereof in which there is one or more hydrocarbon, halo, or other substituents on the aromatic rings.

As used herein the term "alkylarylamino" refers to $(C_6H_5)(alkyl)N$—, or a derivative thereof in which there is one or more hydrocarbon, halo, or other substituents on the aromatic ring, and wherein the alkyl group is straight chain, branched, or cyclic.

I. Preparation of Predominately the β-Anomer of 1,3-Dioxolane Nucleosides

A synthesis of 1,3-dioxolane nucleosides is disclosed that includes condensing a 2-0-protected-5-0-acylated-1,3-dioxolane with a purine or pyrimidine base in the presence of a titanium containing Lewis acid of the structure:

$$TiX_nY_{m-n}$$

wherein m=4; n=2, 3, or 4; Ti=titanium; X=Cl, Br, or I; and Y is alkoxy, aryloxy, amino, alkylamino, dialkylamino, arylamino, diarylamino, alkylarylamino, and mixtures thereof, or a bifunctional molecule that contains both an alkoxy and an amino functional group and that is bound to the titanium molecule by both the alkoxy and amino moieties, to provide predominately the desired β-isomer in the C1'-position of a 1,3-dioxolane nucleoside.

The process can be used to prepare a wide variety of 1,3-dioxolane nucleosides, including those with a cytosine, thymine, uracil, adenine, or guanine base, and alkylated, halogenated, sulfenylated, and alkoxylated derivatives thereof.

Nonlimiting examples of suitable alkoxy groups that can be present in the titanium catalyst include isopropoxide (Oipr), and other lower alkoxy groups (C5 or less). A nonlimiting example of suitable aryloxy groups include phenoxy. Nonlimiting examples of suitable alkylamine and dialkylamine groups that can be present in the titanium catalyst include those with lower alkyl groups (C5 or less). Examples of suitable arylamino groups that can be present in the titanium catalyst include those with phenyl groups. Examples of bifunctional molecules that contain both an alkoxy and an amino functional group and that can be bound to the titanium molecule by both the alkoxy and amino moieties include 2-aminoethanol, 3-aminopropanol, and 1-substituted and 2-substituted derivatives thereof in which the substituents are lower alkyl (C5 or less) or aryl groups.

The condensation reaction can be carried out under any conditions that provide predominately the β-isomer of the 1,3-dioxolane nucleoside. The reaction is typically carried out in a nonprotic, noncoordinating solvent such as toluene, chloroform, dichloromethane, or carbon tetrachloride, at a temperature typically ranging from −80° C. to room temperature (with elevated temperature used if needed to force the reaction). The reaction is monitored by thin layer chromatography until complete. In certain situations, if the product is allowed to remain in the presence of the Lewis acid for too long, epimerization may occur. The product is purified by conventional methods known to those skilled in the art, including chromatography and recrystallization.

The stereoselectivity of these N-glycosylation reactions can be rationalized on the basis of a preferential heteroatom Lewis acid interaction (Scheme 1, below). Use of Lewis acids (e.g., trimethylsilyl trifluoromethanesulfonate) whose role is solely to generate an oxonium ion, should follow Pathway A and result in no stereocontrol. However, in cases where the Lewis acid can pre-complex to a ring heteroatom (i.e., Pathway B), diastereofacial selectivity can be achieved through the minimization of destabilizing 1,2-steric interactions by complexing anti to the protected hydroxymethyl substituent. At the very least, this complexation should dramatically hinder the approach of the silylated base to the α-face. In addition, an intermediate can be formed wherein the associated metal delivers one of its ligands (presumably chloride) to the α-face of the proximal incipient carbonium ion. The resulting α-chloro derivative can then undergo $S_N2$ attack to form the β-N-glycoside.

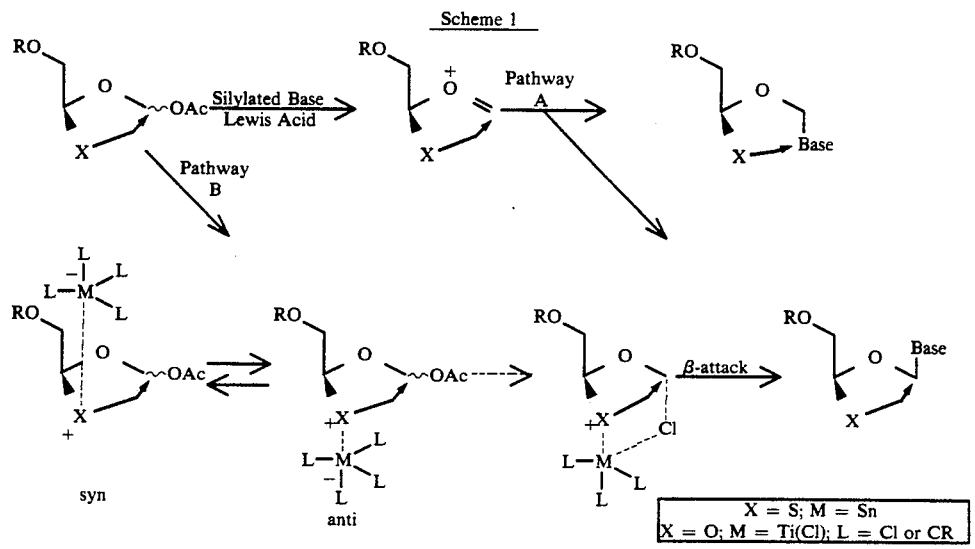

Scheme 1

As examples, β-FDOC, β-DOC and β-DOT can be prepared by coupling a 2-protected hydroxymethyl-4-carboxy-1,3-dioxolane with the appropriate silylated pyrimidine base at ambient temperature using the Lewis acid, TiCl4. Removal of the protecting groups give the free nucleosides β-FDOC, β-DOC, β-DOT or analogues thereof. NMR stereochemical assignments and X-ray structures confirm the β selectivity.

Figure 2:
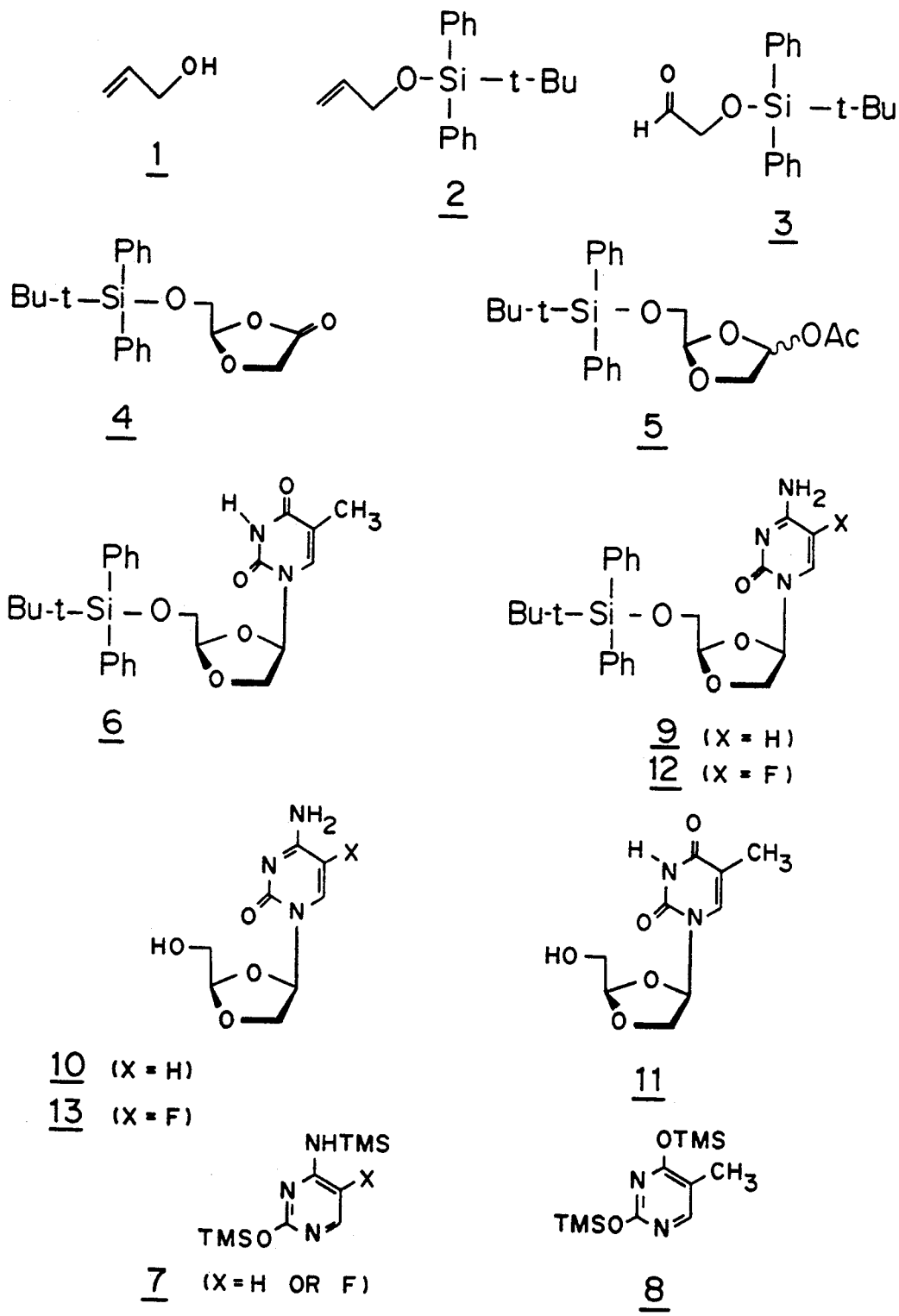
FIG. 2 is an illustration of chemical structures of intermediates used in the reaction scheme for the preparation of 2'-deoxy-3'-oxa-cytidine (DOC, compound 10), 3'-deoxy-3'-oxa-thymidine (DOT, compound 11), and 2'-deoxy-5-fluoro-3'-oxa-cytidine (FDOC, compound 13).

FIG. 2 is an illustration of chemical structures of intermediates used in the reaction scheme set out in detail below for the preparation of 2'-deoxy-3'-oxa-cytidine (DOC, compound 10), 3'-deoxy-3'-oxa-thymidine (DOT, compound 11), and 2'-deoxy-5-fluoro-3'-oxa-cytidine (FDOC, compound 13).

The 1,3-dioxolane ring can be prepared by known methods. In one method, an allyl ether or ester 1 is ozonized (see FIG. 2) to give an aldehyde 3, which reacts with glycolic acid to give a lactone 4. The lactone 4 is treated with a reducing agent such as DIBAL (diisobutylaluminum chloride), Red Al (bis(2-methoxyethoxy)aluminum hydride), and LiAl(O-t-butyl)3H. followed by a carboxylic anhydride, to produce the carboxylate 5. This carboxylate is coupled with a silylated pyrimidine base 8 or a silylated 5-fluoro substituted pyrimidine base 7 in the presence of a titanium containing Lewis acid that can catalyze stereoselective coupling, including TiCl4, TiCl3(OiPr) or TiCl2(OiPr)2, wherein OiPr refers to isopropoxide, to yield the β-isomer of the nucleoside 9 or substituted nucleoside 12 in a high ratio of β:α isomers. The nucleoside 9 or substituted nucleoside 12 is deprotected to produce 10 or 13 or modified at the 5'-position to form a 1,3-dioxolane prodrug analogue.

The term "silylated pyrimidine or purine base", as used herein, refers to a pyrimidine or purine wherein the functional oxygen and nitrogen groups have been protected with suitable silyl moieties. Silyl protecting groups are known to those skilled in the art, and include trialkylsilyl groups of the formula —Si(R1)(R2)(R3) wherein R1, R2, and R3 are lower-alkyl, e.g., methyl, ethyl, butyl, and alkyl possessing 5 carbon atoms or less, or phenyl. Furthermore, R1 can be identical to R2, and R1, R2, and R3 can all be identical. Examples of trialkylsilyl groups include, but are not limited to, trimethylsilyl and t-butyldiphenylsilyl.

As used herein, a leaving group means a functional group that forms an incipient carbocation when it leaves.

Illustrative examples of the synthesis of dioxolane nucleosides according to the present invention are given in Example 1 below.

EXAMPLE 1

Synthesis of Dioxolane Nucleoside

FIG. 2 illustrates the synthesis of 2'-deoxy-3'-oxacytidine (DOC), 2'-deoxy-3'-oxathymidine (DOT), and 2'-deoxy-5-fluoro-3'-oxacytidine (FDOC).

The synthesis of the 1,3-dioxolane moiety begins with allyl alcohol 1. A NaH oil suspension (4.5 g, 60%, 110 mmol) was washed with THF twice (100 ml×2) and the resulting solid suspended in the THF (300 ml). The suspension was cooled to 0° C., allyl alcohol 1 (6.8 ml, 100 mmol) was added dropwise, and the mixture was stirred for 30 minutes at 0° C. t-Butyl-diphenylsilyl chloride (25.8 ml, 100.8 mmol) was added dropwise at 0° C. and the reaction mixture was stirred for 1 hour at 0° C. The solution was quenched with water (100 ml), and extracted with diethyl ether (200 ml×2). The combined extracts were washed with water, dried over MgSO$_4$, filtered, concentrated, and the residue distilled under vacuum (90°–100° C. at 0.5–0.6 mm Hg) to give a colorless liquid 2 (28 g., 94 mmol, 94%). ($^1$H NMR:(CDCl$_3$, 300 MHz) 7.70–7.35 (10H, m, aromatic-H); 5.93 (1H, m, H$_2$); 5.37 (1H, dt, H$_1$) J=1.4 and 14.4 Hz; 5.07 (1H, dt, H$_1$) J=1.4 and 8.7 Hz; 4.21 (2H, m, H$_3$); 1.07 (9H, s, t-Bu)).

The silyl allyl ether 2 (15.5 g, 52.3 mmol) was dissolved in CH$_2$Cl$_2$ (400 ml), and ozonized at −78° C. Upon completion of ozonolysis, DMS (15 ml, 204 mmol, 3.9 eq) was added at −78° C. and the mixture was warmed to room temperature and stirred overnight. The solution was washed with water (100 ml×2), dried over MgSO$_4$, filtered, concentrated, and distilled under vacuum (100°–110° C. at 0.5–0.6 mm Hg) to give a colorless liquid, a silylated glycoaldehyde 3 ((15.0 g, 50.3 mmol, 96%). ($^1$H NMR:(CDCl$_3$, 300 MHz) 9.74 l1H, s, H-CO); 7.70–7.35 (10H, m, aromatic-H); 4.21 (2H, s, —CH$_2$); 1.22 (9H, s, t-Bu)).

Alternative route to Compound 3 bis-t-Butyldiphenylsilyl ether of cis-2-butene-1,3-diol

NaH oil suspension (4.5 g, 60%, 110 mmol) was washed with THF twice (100 ml×2) and the resulting solid suspended in THF (300 ml). The suspension was cooled to 0° C., and to it was added allyl alcohol (6.8 ml, 100 mmol) dropwise, and the mixture was stirred for 0.5 h at 0° C. t-Butyldiphenylsilyl chloride (25.8 ml, 100.8 mmol) was added dropwise at 0° C., and the reaction mixture stirred for 1 h at 0° C. The solution was quenched with water (100 ml), and extracted with ET$_2$O (200 ml×2). The combined extracts were washed with water, dried over MgSO$_4$, filtered, concentrated, and the residue was distilled under vacuum (90°–100° C. at 0.5–0.6 mm Hg) to give a colorless liquid bis-t-butyldiphenylsilyl ether of cis-2-butene-1,3-diol (28 g, 94 mmol, 94%). $^1$H NMR:(CDCl$_3$, 300 MHz) 7.70–7.35 (10H, m, aromatic H), 5.93 (1H, m, H$_2$), 5.37 (1H, dt, H$_1$, J=14.4 Hz), 5.07 (1H, dt, H$_1$, J=1.4 and 8.7 Hz), 4.21 (2H, m, H$_3$), 1.07 (9H, s, t-Bu).

Ozonolysis of bis-t-Butyldiphenylsilyl ether of cis-2-butene-1,3-diol. bis-t-Butyldiphenysilyl ether of cis-2-butene-1,3-diol (15.5 g, 52.3 mmol) was dissolved in CH$_2$Cl$_2$ (400 ml), and ozonized at −78° C. Upon completion of ozonolysis, dimethyl sulfide (15 ml, 204 mmol, 3.9 eq) was added at −78° C., and the mixture was warmed to room temperature and stirred overnight. The solution was washed with water (100 ml×2), dried over MgSO$_4$, filtered, concentrated, and distilled under vacuum (100°–110° C. at 0.5–0.6 mm Hg) to give a colorless liquid aldehyde (15.0 g, 50.3 mmol, 96%).

$^1$H NMR:(CDCl$_3$, 300 MHz) 9.74 ($_1$H, s, H-CO), 7.70–7.35 (10H, m, aromatic H), 4.21 (2H, s, —CH$_2$), 1.22 (9H, s, t-Bu); IR (Neat) 3080, 3060, 2970, 2940, 2900, 2870, 1730, 1470, 1460, 1430, 1390, 1360, 1310, 1200, 1110, 1030, 960, 880, 830, 745, 710.

A portion of the silylated glycoaldehyde 3 (4.0 g, 13.40 mmol) was dissolved in 1,2-dichloroethane (50 ml) and to it was added glycolic acid (1.10 g, 14.46 mmol) in one portion and p-toluenesulfonic acid (0.1 g). The mixture was refluxed for 1 hour. The volume of the solution was then reduced to about half by distilling off the solvent with a Dean-Stark trap. Another 50 ml of dichloroethane was added and the solution refluxed for 30 minutes again. The solution was cooled to room temperature and concentrated under vacuum. The residue was dissolved in ether (200 ml) and the solution washed with NaHCO$_3$ solution (50 ml) and water (50 ml). The combined extracts were dried over MgSO$_4$, filtered, and concentrated to give a colorless oil which gradually solidified under vacuum. Recrystallization from hexane afforded a waxy white solid 4 (2-(t-Butyldiphenylsilyloxy)-methyl-4-oxo-1,3-dioxolane) (4.2 g, 11.78 mmol, 88%). ($^1$H NMR:(CDCl$_3$, 300 MHz) 7.66 and 7.42 (10H, m, aromatic-H), 5.72 (1H, broad, H$_2$), 4.46 (1H, d, 1H$_5$, J=14.4 Hz), 4.28 (1H, d, 1H$_5$, J=14.4 Hz), 3.81 (2H, d, 2CH$_2$O, J=1.8 Hz), 1.04 (9H, s, t-Bu); mp 94–°95° C.; MS (FAB) 357 (M+H), 299, 241, 197, 163, 135, 92; Anal. Calc'd for C$_{20}$H$_{24}$O$_4$Si:C, 67.38; H, 6.79; Found:C, 67.32; H, 6.77).

4-Acetoxy-2-(t-Butyldiphenylsilyloxymethyl)-1,3-dioxolane 29 was prepared using either of the following procedures A or B.

Procedure A:(DIBAL-H) The lactone 4 (1.0 g, 2.81 mmol) was dissolved in toluene (100 ml), and the solution cooled to −78° C. Dibal-H solution (3.0 ml, 1.0M in hexanes, 3 mmol) was added dropwise, while the inside temperature was kept below −70° C. throughout the addition. After the addition was completed, the mixture was stirred for 0.5 hours at −78° C. To it was added Ac$_2$O (5 ml, 53 mmol) and the mixture, with continuous stirring, was allowed to reach room temperature overnight. Water (5 ml) was added to it and the mixture was stirred for 1 hour, MgSO$_4$ (40 g) was then added, and the mixture was stirred vigorously for 1 hour at room temperature. The mixture was filtered, concentrated, and the residue flash chromatographed with 20% EtOAc in hexanes to give a colorless liquid 5 (0.70 g) which was a mixture of the desired acetates and the aldehyde 3 derived from the ring opening reaction.

Procedure B:(LiAlH(OtBu)$_3$) Lactone 4 (451.5 mg, 1.27 mmoles) was dissolved in 6 ml THF (dry), and cooled to −5° C. To this was added 1.7 ml (1.7 mmoles) of a LiAl(OtBu)$_3$H solution (1M in THF; Aldrich) over a 45 minute period. After addition was completed, the mixture was stirred for 7½ hrs. at 0° C. After this time, 1.2 ml (13 mmoles, 10 eq) of dry acetic anhydride was added, followed by 78 mg (0.64 mmoles, 0.5 equiv.) of DMAP (4-dimethylaminopyridine). The reaction was kept at 0° C. for 14 hours, and the quenched at 0° C. by adding 1 ml NaHCO$_3$ and 0.5 g of Na$_2$CO$_3$. The mixture was stirred for 1 hour at 0° C., and then filtered over a 2 inch plug of silica gel (with 6/1-Hexanes/EtOAc), followed by solvent removal to give 930 mg of a yellow oil (1:1.2 ratio at the glycosidic center). Column chromatography (Hexanes/EtOAc, 6/1) gave 332.9 mg of the acetate, which was 90% pure by $^1$H NMR (299.6 mg, 59% yield). ($^1$H NMR:(CDCl$_3$, 300 MHz) 1.02 (s, 9H, major isomer), 1.04 (s, 9H, minor isomer), 1.96 (s, 3H, minor), 2.12 (s, 3H, major), 3.7 (m, 2H), 4.07 (m, 2H), 5.24 (t, 1H, minor, J=4.2 Hz), 5.37 (t, 1H, major, J=3 Hz), 6.3 (t, 1H, minor, J=3.9 Hz), 6.37 (dd, 1H, major, J=1.5 Hz, J=4.5 Hz), 7.39 (m, 6H), 6.67 (m, 4H). IR (neat):cm$^{-1}$ 3090, 2980, 2880, 1760, 1475, 1435, 1375, 1240, 1120, 1000. MS (FAB, Li+):407(M+Li), 312, 282, 241, 197, 162, 125. Anal. Calc. for C$_{22}$H$_{28}$O$_5$Si:C, 65.97%, H, 7.05%; Found:C, 66.60%, H, 7.27%).

The crude acetate 5 (0.25 g, 0.62 mmol, quantity assumed with 0.50 g of the previous mixture) was dissolved in methylene chloride (50 ml), and to it the silylated cytosine 7 (X=H) (0.10 g, 0.63 mmol) was added in one portion. The mixture was stirred for 10 minutes, and to it a TiCl$_4$ solution (1.30 ml, 1.0M solution in CH$_2$Cl$_2$, 1.30 mmol) was added, dropwise, at room temperature. It took 2 hours to complete the reaction. Upon completion, the solution was concentrated, the residue was triturated with pyridine (2 ml) and subjected to flash chromatography (first with neat EtOAc then 20% EtOH in EtOAc) to give a tan solid, which was further recrystallized to give a white crystalline solid 9 (0.25 g, 0.55 mmol, 89%). ($^1$H NMT (CDCl$_3$, 300 MHz) 7.97 (1H, d, H$_6$, J=7.8 Hz), 7.67 and 7.40 (10H, m, aromatic-H), 6.24 (1H, d, H$_{1'}$), 5.62 (1H, d, H$_5$, J=7.6 Hz), 5.03 (1H, t, H$_{4'}$), 4.20 (1H, dd, 1H$_{2'}$, J=1.2 and 9.0 Hz), 4.15 (1H, dd, 1H$_{2'}$, J=4.8 and 9.0 Hz), 3.96 (1H, dd, 1H$_{5'}$, J=2.1 and 8.7 Hz), 3.93 (1H, dd, 1H$_{5'}$, J=2.1 and 8.7 Hz), 1.08 (9H, s, t-Bu).)

Silylether 9 (0.12 g, 0.27 mmol) was dissolved in THF (20 ml), and an n-Bu$_4$NF solution (0.30 ml, 1.0M solution in THF, 0.30 mmol) was added, dropwise, at room temperature. The mixture was stirred for 1 hour and concentrated under vacuum. The residue was taken up with EtOH/pyridine (2 ml/2 ml), and subjected to flash chromatography (first with EtOAc, then 20% EtOH in EtOAc) to afford a white solid, which was further recrystallized from EtOH to give a white crystalline solid 33 (DOC) (55 mg, 0.26 mmol, 96%). ($^1$H NMR:(DMSO-d$^6$, 300 MHz) 7.79 (1H, d, H$_6$, J=7.5 Hz), 7.18 and 7.11 (2H, broad, NH$_2$), 6.16 (1H, dd, H$_{1'}$, J=3.0and 4.2 Hz), 5.70 (1H, d, H$_5$, J=7.5 Hz), 5.16 (1H, t, OH, J=6.0 Hz), 4.91 (1H, t, H$_{4'}$, J=2.7 Hz), 4.05 (2H, m, H$_{2'}$), 3.62 (2H, m, 2H$_{5'}$); mp 183°-184° C.

The coupling reaction of acetate 5 with silylated thymine 8 showed a titanium species dependent selectivity in accordance with the following observations (ratios were determined by $^1$H NMR of the crude reaction mixtures):

| Titanium Species | β:α Ratio |
|---|---|
| TiCl$_4$ | 7:1 |
| TiCl$_3$(OiPr) | 10.1 |
| TiCl$_2$(OiPr)$_2$ | >98:2 |

In the coupling reaction using TiCl$_3$(OiPr), the impure acetate 5 from the procedure B reduction above (assumed 69% of the mixture, 185.4 mg, 0.4653 mmol) was dissolved in 8 ml of dry dichloromethane along with 144 mg (1.15 eq) of silylated thymine 8, and this mixture was stirred under argon at room temperature. Next 0.57 ml (1.15 eq) of a freshly prepared solution of TiCl$_3$(OiPr) in dichloromethane (1M solution prepared from 2 eq of TiCl$_4$ and 1 eq of TiCl(OiPr)$_3$) was added dropwise over a 25 minute period. After 2.5 hours, 0.07 ml (0.15 eq) of a TiCl$_4$/dichloromethane solution (1M, Aldrich Chemical Company, Milwaukee, Wis.) was added and the reaction was stirred for an additional hour. Then 3 ml of ethanol and 5 ml of NaHCO$_3$ solution were added, stirred for 10 minutes, followed by extraction with additional NaHCO$_3$ solution. The aqueous layer was separated, washed twice with 100 ml of dichloromethane, and the organic layers were combined and dried over MgSO$_4$. Filtration, solvent removal, column chromatography (⅓:Hexanes/EtOAc), and then recrystallization (1/1:Hexanes Et$_2$O) gave 160 mg (74%) of compound 6 as a white powder. ($^1$H NMR:CDCl$_3$, 300 MHz) 1.06 (s, 9H), 1.68 (s, 3H), 3.91 (t, 2H, J=3.3 Hz), 4.14 (d, 2H, J=3.9 Hz), 5.06 (t, 1H, J=3.3 Hz), 6.34 (t, 1H, J=3.9 Hz), 7.4 (m, 6H), 7.7 (m, 4H), 8.62 (bs, 1H). MS (FAB, Li+):473 (M+Li), 409, 307, 241, 197, 154, 127. Anal. Calc. for C$_{25}$H$_{30}$O$_5$N$_2$Si:C, 64.35%; H, 6.48%; N, 6.00%; Found:C, 64.42%; H, 6.52%; N, 5.97%.

Alternative Procedure 1.156 g (70% by $^1$H NMR, 0.809 g, 2.02 mmoles) of the acetate from Procedure B was dissolved in 25 ml of CH$_2$Cl$_2$ with 640 mg (1.15 equiv.) of silylated fluorocytosine. Next, 2.222 mmoles of TiCl$_3$(OiPr) was added as a solution with 6 ml CH$_2$Cl$_2$ (see previous experimental for TiCl$_3$(OiPr) preparation), over a 70 minute period. After 2 hours total time, 1.1 ml of TiCl$_4$/CH$_2$Cl$_2$ (1 ml solution, Aldrich, 0.55 equiv.) was added over 45 minutes. This mixture was then stirred for 16 hours, and then an additional 0.3 ml. of TiCl$_4$/CH$_2$Cl$_2$ was added with stirring for 2 more hours. The mixture was then sequentially quenched with 20 ml of hours. The mixture for 30 minutes, followed by filtration over 2 inches of silica gel with 6/1-EtOAc/EtOH, followed by solvent removal gave 1.28 g of a yellowish form (9:1 β:α by $^1$H NMR). Column Chromatography (6/1-EtOAc/EtOH) gave 490 mg (52% yield) of the coupled product as a white powder.

In the coupling reaction using TiCl$_2$(OiPr)$_2$, impure acetate from the procedure B reduction (assumed 50% of the mixture, 444 mg, 1.11 mmol) was dissolved in 18 ml of dry dichloromethane along with 654.1 mg of silylated thymine 8 and stirred at room temperature under argon. Next, 1.3 ml of a 2M TiCl$_2$(OiPr)$_2$/CH$_2$/Cl$_2$ solution was added over a 20 minute period. After 14 hours, 1 ml of a 1M TiCl$_4$/CH$_2$Cl$_2$ solution was added and the reaction was stirred for an additional 3 hours. Then 4 ml of concentrated NH$_4$OH was added, along with 10 ml of dichloromethane. Ten minutes of stirring followed by filtration over 1 inch of silica gel with EtOAc, solvent removal and then column chromatography of the resulting oil gave 164.9 mg (32%) of compound 10.

The silyl ether 6 (60.9 mg, 0.131 mmol) was dissolved in 2 ml of THF and 0.14 ml of a Bu$_4$NF/THF solution (1M, Aldrich was added. After stirring for 24 hours, the solvent was removed in a vacuum and column chromatography (5/1:EtOAc/EtOH) of the resulting oil gave 22.6 mg (76%) of the desired nucleoside 11 (DOT) as a white powder. ($^1$H NMR:(HOD (4.8 ppm),, 300MHz) 1.83 (s, 3H), 3.82 (m, 2H), 4.18 (dd, 1H, J=10.5 Hz, J=6 Hz), 5.06 (s, 1H), 6.33 (d, 1H, J=5.7 Hz), 7.72 (s, 1H).

The impure acetate 5 from the procedure B reduction above (assumed 80% by $^1$H NMR analysis, 117.6 mg, 0.294 mmol) and 20.8 mg (1.5 eq) of silylated fluorocytosine 7 (X=F) were dissolved in 10 ml of dry dichloromethane. Then 0.59 ml (2 eq) of a TiCl$_4$/dichloromethane solution was added dropwise over 1 hour. After stirring for 30 additional minutes, 5 ml of dichloromethane and 1 ml of concentrated NH$_4$OH were added, the solvent was removed in a vacuum, and column chromatography (EtOAc/EtOH:1/1) gave 35 mg (25%) of compound 12 as a white solid. ($^1$H NMR:(CDCl$_3$, 300 MHz) 1.06 (s, 9H), 3.62 (dq, 2H, J=2.7 Hz, J=12.3 Hz), 3.9 (m, 2H), 5.01 (t, 1H, J=2.4 Hz), 6.2 (m, 1H), 7.41 (m, 6H), 7.7 (m, 4H), 7.92 (d, 1H, J=6 Hz).)

The silyl ether 12 (116.8 MG, 0.249 mmol) was dissolved in 3 ml of dry THF, and 0.3 ml of a Bu$_4$NF/THF solution (1M, Aldrich Chemical Company, Milwaukee, Wis.) was added. After 3 hours of stirring, the solvent was removed by vacuum, and column chromatography (EtOAc/EtOH:4/1) gave 48.1 mg (84%) of the nucleoside 13 (FDOC) as a white powder. ($^1$H NMR:(DMSO-d$^6$, 300 MHz) 3.63 (m, 2H), 4.01 (dd, 1H, J=5.1 Hz, J=9.6 Hz), 4.08 (d, 1H, J=9.6 Hz), 4.87 (s, 1H), 5.26 (t, 1H, J=6 Hz), 6.07 (m, 1H), 7.49 (bs, 1H), 7.73 (bs, 1H), 8.12 (d, 1H, J=7.2 Hz).)

II. Process for the Resolution of C4'-Racemic Mixtures of 1,3-Dioxolane Nucleosides A method is provided for the resolution of racemic mixtures of C4'-nucleoside enantiomers of 1,3-dioxolane nucleosides. The method involves the use of enzymes for which one enantiomer is a substrate and the other enantiomer is not. The enzyme catalyses the reaction in the "recognized" enantiomer, and then the reacted enantiomer is separated from the unreacted enantiomer on the basis of the new difference in physical structure. Given the disclosure herein, one of skill in the art will be able to choose an enzyme that is selective for the nucleoside enantiomer of choice (or selective for the undesired enantiomer, as a method of eliminating it), by selecting of one of the enzymes discussed below or by systematic evaluation of other known enzymes. Given this disclosure, one of skill in the art will also know how to modify the substrate as necessary to attain the desired resolution. Through the use of either chiral NMR shift reagents or polarimetry, the optical enrichment of the recovered ester can be determined.

The following examples further illustrate the use of enzymes to resolve racemic mixtures of enantiomers. Other known methods of resolution of racemic mixtures can be used in combination with the method of resolution disclosed herein. All of these modifications are considered within the scope of the invention. The following examples are not intended to limit the scope of the invention.

Resolution Based on Hydrolysis of C5'-Nucleoside Esters

In one embodiment, the method includes reacting the C5'-hydroxyl group of a mixture of 1,3-dioxolane nucleoside racemates with an acyl compound to form C5'-esters in which the nucleoside is in the "carbinol" end of the ester. The racemic mixture of nucleoside C5'-esters is then treated with an enzyme that preferentially cleaves, or hydrolyses, one of the enantiomers and not the other.

An advantage of this method is that it can be used to resolve a wide variety of nucleosides, including pyrimidine and purine nucleosides that are optionally substituted in the carbohydrate moiety or base moiety. The broad applicability of this method resides in part on the fact that although the carbinol portion of the ester plays a role in the ability of an enzyme to differentiate enantiomers, the major recognition site for these enzymes is in the carboxylic acid portion of the ester. Further, one may be able to successfully extrapolate the results of one enzyme/substrate study to another, seemingly-different system, provided that the carboxylic acid portions of the two substrates are the same or substantially similar.

Another advantage of this method is that it is regioselective. Enzymes that hydrolyse esters typically do not catalyze extraneous reactions in other portions of the molecule. For example, the enzyme lipase catalyses the hydrolysis of the ester of 2-hydroxymethyl-5-oxo-1,3-oxathiolane without hydrolysing the internal lactone. This contrasts markedly with "chemical" approaches to ester hydrolysis.

Still another advantage of this method is that the separation of the unhydrolysed enantiomer and the hydrolysed enantiomer from the reaction mixture is quite simple. The unhydrolysed enantiomer is more lipophilic than the hydrolysed enantiomer and can be efficiently recovered by simple extraction with one of a wide variety of nonpolar organic solvents or solvent mixtures, including hexane and hexane/ether. The less lipophilic, more polar hydrolysed enantiomer can then be obtained by extraction with a more polar organic solvent, for example, ethyl acetate, or by lyophilization, followed by extraction with ethanol or methanol. Alcohol should be avoided during the hydrolysis because it can denature enzymes under certain conditions.

Enzymes and Substrates

With the proper matching of enzyme and substrate, conditions can be established for the isolation of either nucleoside enantiomer. The desired enantiomer can be isolated by treatment of the racemic mixture with an enzyme that hydrolyses the desired enantiomer (followed by extraction of the polar hydrolysate with a polar solvent) or by treatment with an enzyme that hydrolyses the undesired enantiomer (followed by removal of the undesired enantiomer with a nonpolar solvent).

Enzymes that catalyze the hydrolysis of esters include esterases, for example pig liver esterase, lipases, including porcine pancreatic lipase and Amano PS-800 lipase, substillisin, and α-chymotrypsin.

The most effective acyl group to be used to esterify the C5'-position of the nucleoside can be determined without undue experimentation by evaluation of a number of homologs using the selected enzyme system. For example, when 1,3-oxathiolane nucleosides are esterified with butyric acid, resolutions with both pig liver esterase and Amano PS-800 proceed with high enantioselectivity (94-100 enantiomeric excess) and opposite selectivity. Non-limiting examples of other acyl groups that can be evaluated for use with a particular nucleoside enantiomeric mixture and particular enzyme include alkyl carboxylic acids and substituted alkyl carboxylic acids, including acetic acid, propionic acid, butyric acid, and pentanoic acid. With certain enzymes, it may be preferred to use an acyl compound that is significantly electron-withdrawing to facilitate hydrolysis by weakening the ester bond. Examples of electron-withdrawing acyl groups include α-haloesters such as 2-chloropropionic acid, 2-chlorobutyric acid, and 2-chloropentanoic acid. α-Haloesters are excellent substrates for lipases.

Resolution Conditions

The enzymatic hydrolyses are typically carried out with a catalytic amount of the enzyme in an aqueous buffer that has a pH that is close to the optimum pH for the enzyme in question. As the reaction proceeds, the pH drops as a result of liberated carboxylic acid. Aqueous base should be added to maintain the pH near the optimum value for the enzyme. The progress of the reaction can be easily determined by monitoring the change in pH and the amount of base needed to maintain pH. The hydrophobic ester (the unhydrolysed enantiomer) and the more polar alcohol (the hydrolysed enantiomer) can be sequentially and selectively extracted from the solution by the judicious choice of organic solvents. Alternatively, the material to be resolved can be passed through a column that contains the enzyme immobilized on a solid support.

Enzymatic hydrolyses performed under heterogeneous conditions can suffer from poor reproducibility. Therefore, it is preferred that the hydrolysis be performed under homogeneous conditions. Alcohol solvents are not preferred because they can denature the enzymes. Cosolvents that do not denature enzymes should be used, such as acetonitrile. Homogeneity can be achieved through the use of non-ionic surfactants, such as Triton X-100. However, addition of these surfactants not only assists in dissolving the starting material, they also enhances the aqueous solubility of the product. Therefore, although the enzymatic reaction can proceed more effectively with the addition of a non-ionic surfactant than under heterogeneous conditions, the isolation of both the recovered starting material and the product can be made more difficult. The product can be isolated with appropriate chromatographic and chemical (e.g., selective salt formation) techniques. Diacylated nucleosides can be used but are often quite lipophilic and hard to dissolve in the medium used.

Modifications and variations of the present invention will be obvious to those skilled in the art from the foregoing detailed description of the invention. Such modifications and variations are intended to come within the scope of the appended claims. The references cited above are hereby incorporated by reference to more fully describe the invention.

I claim:

1. A process for the preparation of 1,3-dioxolane nucleosides comprising reacting a 2-0—protected-5-0-acylated-1,3-dioxolane with an oxygen or nitrogen protected purine or pyrimidine base in the presence of a titanium catalyst of the formula:

$$TiX_nY_{m-n}$$

wherein m=4; n=2, 3, or 4; Ti=titanium; X=Cl, Br, or I; and Y is alkoxy, amino, alkylamino, dialkylamino, arylamino, diarylamino, alkylarylamino, and mixtures thereof, or a bifunctional molecule that contains both an alkoxy and an amino bifunctional group and that is bound to the titanium molecule by both the alkoxy and amino moieties, to provide predominately the desired β-isomer in the C1'-position of the 1,3-dioxolane nucleoside.

2. The method of claim 1, wherein the titanium catalyst is selected from the group consisting of TiCl$_4$, TiCl$_2$(OiPr)$_2$, and TiCl$_3$(OiPr).

3. The method of claim 1, wherein the 1,3-dioxolane nucleoside is 2-hydroxymethyl-5-(thymidin-1-yl)-1,3-dioxolane.

4. The method of claim 1, wherein the purine of pyrimidine base is selected form the group consisting of cytosine, thymine, uracil, adenine, and guanine.

5. The method of claim 1, wherein the alkoxy group is lower alkoxy (C$_5$ or less).

6. The method of claim 1, wherein the alkyl moiety in the alkylamino group has one to five carbon atoms.

7. The method of claim 1, wherein the bifunctional molecule is selected from the group consisting of 2-aminoethanol, 3-aminopropanol, and 1-substituted and 2-substituted derivatives thereof in which the substituents are lower alkyl (C$_5$ or less) or aryl groups.

8. The method of claim 1, wherein the titanium catalyst is TiCl$_4$.

9. The method of claim 1, wherein the alkyl group contains one to five carbon atoms.

10. The method of claim 1, wherein the 1,3-dioxolane nucleoside is 2-hydroxymethyl-5-(5-fluorocytosin-1-yl)-1,3-dioxolane.

* * * * *